United States Patent
Buss

(10) Patent No.: US 10,188,524 B2
(45) Date of Patent: Jan. 29, 2019

(54) ROTATIONAL DRIVE MECHANISM, TOOL AND METHODS FOR USING SAME

(71) Applicant: AESCULAP IMPLANT SYSTEMS, LLC, Center Valley, PA (US)

(72) Inventor: Donald A. Buss, Center Valley, PA (US)

(73) Assignee: AESCULAP IMPLANT SYSTEMS, LLC, Center Valley, PA (US)

( * ) Notice: Subject to any disclaimer, the term of this patent is extended or adjusted under 35 U.S.C. 154(b) by 274 days.

(21) Appl. No.: 14/840,876

(22) Filed: Aug. 31, 2015

(65) Prior Publication Data

US 2017/0056192 A1   Mar. 2, 2017

Related U.S. Application Data

(63) Continuation of application No. 14/839,486, filed on Aug. 28, 2015.

(51) Int. Cl.
| | | |
|---|---|---|
| *A61F 2/44* | (2006.01) | |
| *A61F 2/46* | (2006.01) | |
| *A61B 17/80* | (2006.01) | |
| *A61F 2/30* | (2006.01) | |

(52) U.S. Cl.
CPC ............ *A61F 2/442* (2013.01); *A61B 17/808* (2013.01); *A61F 2/447* (2013.01); *A61F 2/4611* (2013.01); *A61F 2002/3039* (2013.01); *A61F 2002/30242* (2013.01); *A61F 2002/30579* (2013.01); *A61F 2002/30841* (2013.01); *A61F 2002/30878* (2013.01); *A61F 2002/4619* (2013.01); *A61F 2002/4627* (2013.01); *A61F 2220/0016* (2013.01)

(58) Field of Classification Search
CPC ...... A61F 2/4455; A61F 2/446; A61F 2/4465; A61F 2/447; A61F 2/4611; A61F 2/44; A61F 2/442
USPC ............................................. 623/17.11–17.16
See application file for complete search history.

(56) References Cited

U.S. PATENT DOCUMENTS

| | | | |
|---|---|---|---|
| 6,527,803 B1 * | 3/2003 | Crozet | A61F 2/442 606/31 |
| 8,597,353 B2 * | 12/2013 | Kana | A61F 2/4455 606/246 |
| 2005/0049590 A1 | 3/2005 | Alleyne et al. | |

\* cited by examiner

*Primary Examiner* — Si Ming Ku
(74) *Attorney, Agent, or Firm* — Kenealy Vaidya LLP

(57) ABSTRACT

The disclosed subject matter relates a medical instrument having a rotational drive mechanism that can be integrated into a variety of medical devices, including a tool used as an external retaining ring removal tool or as a non-marring bushing inserter, or in a spinal interbody device. The tool can include a knob portion at a proximal end and a drive mechanism at the distal end. The drive mechanism can include a plurality of drive pins that can be actuated to extend outward by rotating the knob portion. The spinal interbody device can include a drive mechanism configured to translate rotational motion into a linear driving motion to cause locking projections to move into engagement with vertebrae.

17 Claims, 13 Drawing Sheets

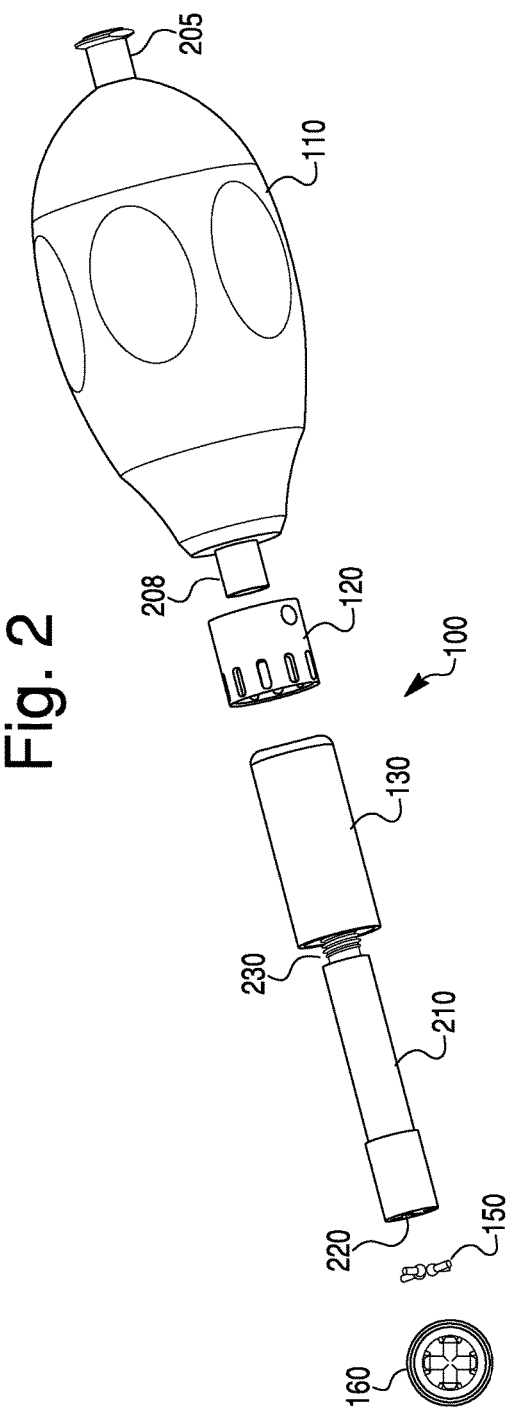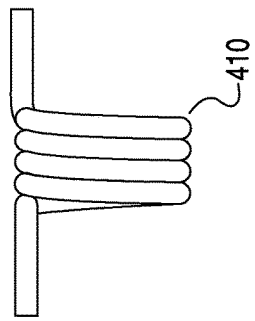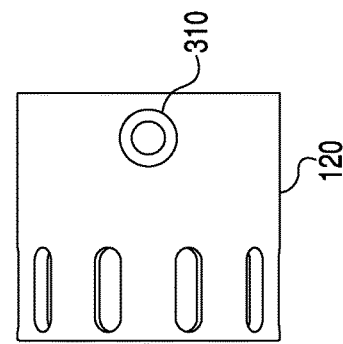

ROTATIONAL DRIVE MECHANISM, TOOL AND METHODS FOR USING SAME

BACKGROUND

1. Field

The presently disclosed subject matter relates generally to a rotational drive mechanism that can be used for a variety of medical device applications.

2. Description of the Related Art

Surgical procedures are generally performed in an operating field that is typically confined to a small area. This can restrict the use of various tools to sub-optimal angles that can produce side loads, reduce visibility, as well as potentially damage the medical devices that are being manipulated. Many conventional medical instruments do not provide ease of use, ease of cleaning and sterilization along with the ability to perform multiple tasks.

SUMMARY

Accordingly, it may be beneficial to provide an instrument having a drive mechanism that allows various components to be manipulated without damaging or contaminating those components. The disclosed embodiments provide an instrument having a rotational drive mechanism that can be incorporated into a variety of medical instruments, including a tool used as an external retaining ring removal tool or as a non-marring bushing inserter, or as a spinal interbody device.

According to one aspect of the disclosed subject matter, an instrument is provided having a drive mechanism configured to translate rotational motion of a handle into a linear driving motion of drive pins via a first housing structure having spiral cam slots and a second housing structure having linear cam slots. The instrument can include drive pins that extend in a radial direction away from a central longitudinal axis and away from an outermost radial surface of the instrument to allow engagement of the instrument with a work piece or an internal snap ring.

In one embodiment, the disclosed drive mechanism translates rotary motion of the proximal handle into a linear driving action driving drive pins out of and away from the drive mechanism. The working mechanism can involve a rotating cam plate coupled to a stationary housing with the drive pins sandwiched there between. The stationary housing can include linear pin slots in which the drive pins ride. The rotating cam plate can include spiral ball slots in which the drive pins also ride. Within these slots, each of the drive pins can be guided in a linear inward and outward radial motion.

According to another aspect of the disclosed subject matter, a medical instrument is provided that includes a handle, a primary housing structure located adjacent the handle and having one of a spiral ball slot and a substantially linear pin slot, a secondary housing structure located adjacent the primary housing structure and having a substantially linear pin slot if the primary housing has a spiral ball slot and having a spiral ball slot if the primary housing has a substantially linear pin slot and at least one pin located in the spiral ball slot and the linear pin slot.

According to another aspect, a medical instrument is provided having a central axis that includes a handle having a proximal end and an opposed distal end, a first housing structure located at the distal end and rotatable with respect to the handle and at least one drive pin configured to extend in a radial direction away from the central axis of the medical device and away from an outermost radial surface of the first housing structure to allow engagement of the medical device with a work piece.

According to another aspect, a medical instrument is provided having a central axis that includes a handle having a proximal end and an opposed distal end, a plurality of drive pins operatively connected with the handle, each of the drive pins having a pin central axis, a cam structure located between the handle and the drive pins and configured to move the drive pins outward and along each pin central axis in a direction substantially perpendicular to the central axis of the medical device.

In one embodiment, the disclosed instrument can be used for insertion and removal of a foot plate member which is part of a vertebral body replacement device. An exemplary foot plate is disclosed in commonly assigned U.S. Pat. Nos. 8,182,537; 8,591,587; and 8,690,950.

According to another aspect of the disclosed subject matter, a spinal interbody device and system is provided which incorporates a drive mechanism for extending and retracting one or more locking projections. According to this aspect, the drive mechanism is configured to translate rotational motion into a linear driving motion to cause locking projections to move into engagement with vertebrae via a first structure having spiral cam slots and a second structure having linear cam slots. According to this aspect, a medical instrument, such as a spinal interbody device is provided having a front surface, a rear surface substantially opposed to the front surface, an upper surface connected to the front and rear surface, a lower surface opposed to the upper surface and connected to each of the front and rear surfaces, at least one opening formed at the front surface, the opening extending through the interbody device, at least one projection and a drive mechanism disposed adjacent the at least one opening and configured to move the at least one projection so that the projection moves through at least one of the upper surface or the lower surface.

According to another aspect, the drive mechanism includes a front cam plate having at least one of a linear cam slot and a curved cam slot for engaging the at least one projection.

According to another aspect, the opening extends through the interbody device to the rear surface and the drive mechanism includes a drive bar that extends from the at least one opening disposed on the front surface of the interbody device to the rear surface of the interbody device.

According to still another aspect, at least one linear slot is located in at least one of the cam plate and the at least one opening formed in the front surface of the interbody device.

According to another aspect, at least one projection is located within the curved cam slot and the linear cam slot.

According to another aspect, at least one of a linear cam slot and a curved cam slot is located at an opening formed in the rear surface of the interbody device.

BRIEF DESCRIPTION OF THE DRAWINGS

The disclosed subject matter of the present application will now be described in more detail with reference to exemplary embodiments of the apparatus and method, given by way of example, and with reference to the accompanying drawings, in which:

FIG. 2 is an exploded perspective view of the mechanism of FIG. 1;

FIG. 3 is side view of a spring capture sleeve in accordance with the disclosed subject matter;

FIG. 4 is a front view of a spring which is incorporated into the spring capture sleeve in accordance with the disclosed subject matter;

DETAILED DESCRIPTION OF EXEMPLARY EMBODIMENTS

Figure 1:
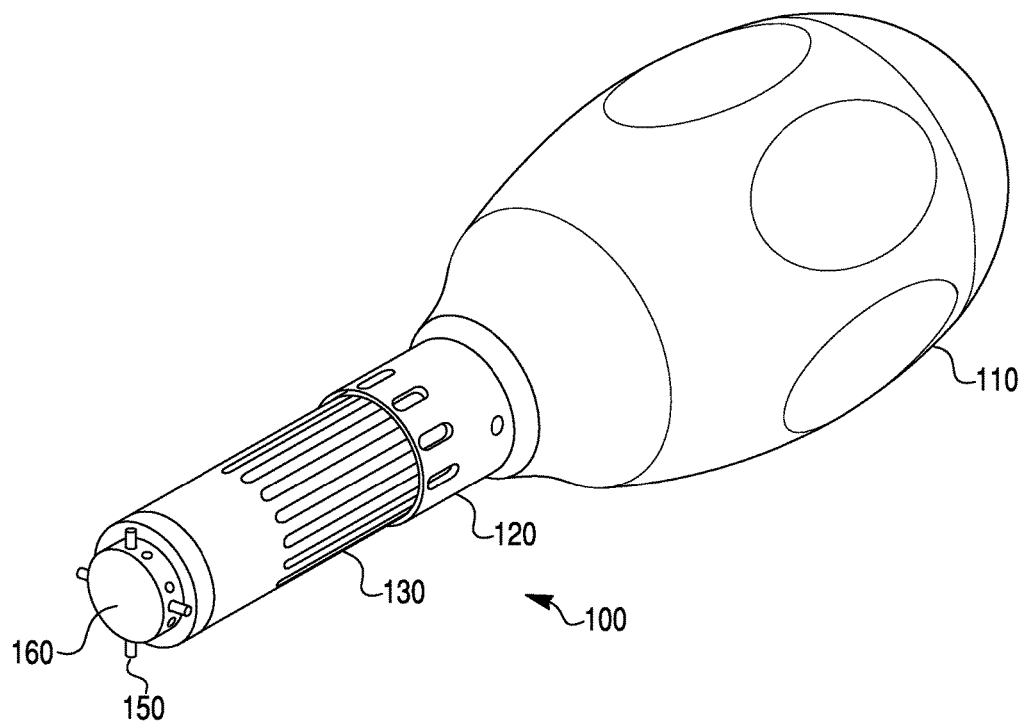
FIG. 1 is a perspective view of an exemplary embodiment of a ball drive mechanism in accordance with the disclosed subject matter.

FIG. 1 is a perspective view of one embodiment of the drive mechanism made in accordance with principles of the disclosed subject matter. The mechanism 100 can be used in any suitable configuration for a variety of procedures, including as an external ring removal tool and a non-marring bushing inserter. In one embodiment, the mechanism 100 can be used as a surgical tool in conjunction with other medical devices. However, the mechanism 100 can also be configured to work with a variety of non-medical tools and can be used to insert or remove prosthetic devices as well as other orthopedic devices.

It should be understood that the term "proximal" as used throughout this description references a direction towards a user of the device and "distal" references a direction away from the user and towards the component to be engaged by the mechanism 100.

As shown in FIG. 1, the mechanism 100 includes a handle shaped as a knob portion 110 formed at a proximal end of the mechanism 100, the knob portion 110 having a size and shape that allows a user to easily rotate the knob in order to facilitate operation of the mechanism 100. The knob portion 110 is fitted against a spring capture sleeve 120 that facilitates operation of the mechanism as will be described in greater detail below. The spring capture sleeve 120 is fitted against a capture sleeve 130 that servers to cover a drive barrel (not shown in FIG. 1). FIG. 1 also shows that the mechanism 100 terminates at a follower plate 160. The follower plate 160 houses one or more drive pins 150. In operation, rotational motion of the knob portion 110 is translated to a linear drive action that actuates the drive pins 150 so that they extend in a direction away from a central axis of the mechanism 100 (which happens to coincide with the rotational axis of the knob portion 110 in this embodiment). The mechanism 100 is considered to be in a "locked" or "extended" state when the drive pins 150 are extended outward as shown in FIG. 1. Rotation of the knob portion 110 in an opposite direction causes the drive pins to be retracted within the body of the follower plate (e.g., in a direction towards the central axis of the mechanism 100). The mechanism is considered to be in an "unlocked" or "non-extended" state when the drive pins 150 have been retracted into the body of the follower plate 160.

FIG. 2 is an exploded perspective view of the mechanism 100. As shown in FIG. 2, a luer lock 205 is disposed along the central or rotational axis of the knob portion 110. The luer lock 205 is a cleaning port that is used to clean out the mechanism 100. Screw receiving threads (not shown in FIG. 2) can be formed on an interior surface of the distal end 208 of the luer lock 205. FIG. 2 also shows the spring capture sleeve 120 which will be described in greater detail below and the capture sleeve 130 which is fitted against the spring capture sleeve 120. FIG. 2 also shows a drive barrel 210 having threads 230 formed on a proximal end and a cam plate 220 formed on a distal end. The drive barrel 210 extends along the central axis of the mechanism and is disposed within the capture sleeve 130 and the spring capture sleeve 120. Thus, when the mechanism is operational, the drive barrel is generally not visible to the user. The threads 230 formed at the proximal end of the drive barrel 210 can engage the interior threads formed at the distal end 208 of the rotational knob 110.

FIG. 2 also shows a cam plate 220 formed on the distal end of the drive barrel 210. The cam plate 220 will be described in greater detail below, and can include a plurality of spiral (or otherwise grooved) ball slots that are configured to receive and engage at least a part of the drive pins 150. FIG. 2 also shows a follower plate 160 which can be attached to the distal end of the mechanism 100 and which includes a plurality of linear ball slots for retaining and guiding the drive pins 150 during actuation of the device. As will be described in greater detail below, the follower plate 160 can be fitted to the end of the drive barrel 210 through a variety of mechanisms, including by mutually engaging screw threads that can be formed on the follower plate 160 and on an interior surface of the drive barrel 210. Alternatively, the follower plate 160 can be press fitted into the end of the drive barrel 210.

FIG. 3 shows a side view of the spring capture sleeve 120, which includes an opening 310. The drive barrel 210 extends through the spring capture sleeve 120 in order for the threads 230 at the end of the drive barrel 210 to engage the threads (not shown) formed at the distal end 208 of the knob portion 110. The spring capture sleeve 120 also includes a spring 410 (FIG. 4), which is fitted within the spring capture sleeve 120. The spring 410 shown in FIG. 4 is configured to maintain the position of the drive pins 150, either in a fully extended position or in a fully retracted position. In one embodiment, the opening 310 is used with a set screw to secure the spring capturing sleeve 120 to the drive barrel 210 after the spring 410 has been pre-tensioned to the desired spring load, then the spring capturing sleeve 120 is welded and further pinned to the drive barrel 210.

Figure 5:
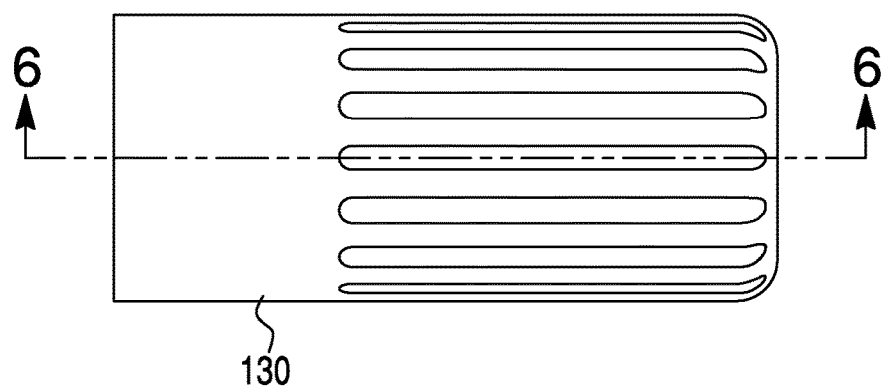
FIG. 5 is a side view of a capture sleeve in accordance with the disclosed subject matter.

FIG. 5 shows a side view of the capture sleeve 130. As described above, the capture sleeve 130, fits over the drive barrel 210 so that the drive barrel 210 passes through a hollow passage formed within the capture sleeve 130. Although not illustrated, it is within the scope of this invention to form screw receiving threads along an interior surface at the distal end of the drive barrel 210.

Figure 6:
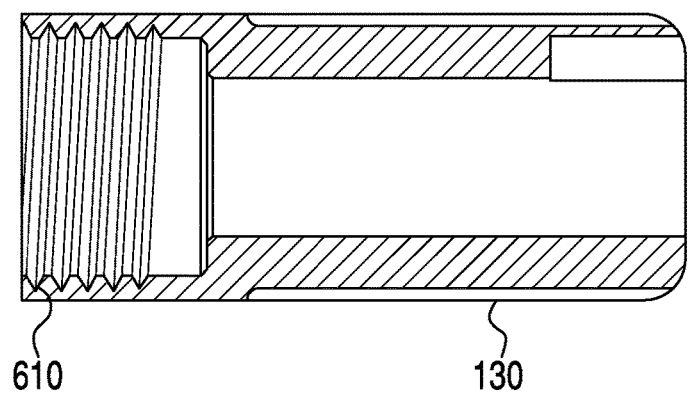
FIG. 6 is a cross-sectional view of the capture sleeve taken along line 6-6 in FIG. 5.

FIG. 6 is a cross-sectional view of the capture sleeve 130 taken along line 6-6 shown in FIG. 5. In the upper right corner of the capture sleeve 130 illustrated in FIG. 6, a cutout is defined in which the torsion spring 410 is secured. FIG. 6 also shows the threads 610 formed on the interior surface at a distal end of the capture sleeve 130. The threads 610 are configured to threadably engage threads (not shown) formed on the follower plate 160 so that the follower plate 160 is securely held in contact with the distal end of the drive barrel 210, and more specifically, so that the drive pins 150 are placed in engagement with spiral ball slots formed on the cam plate 220 which is disposed on a distal end on the drive barrel 210. When the follower plate 160 threadably engages the threads 610 of the capture sleeve 130, the drive barrel 210 is then retained within the capture sleeve 130 and the spring capture sleeve 120.

Figure 7A:
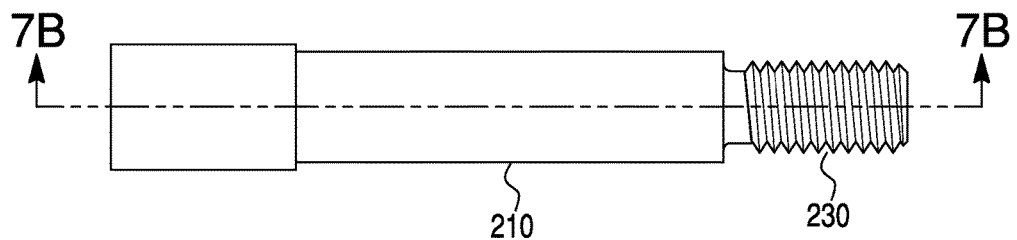
FIG. 7A is a side view of a drive barrel in accordance with the disclosed subject matter.

FIG. 7A shows a side view of the drive barrel 210. The drive barrel 210, in accordance with the embodiment of FIG. 7A, is generally tubular in shape and includes threads 230 formed at its proximal end. The threads 230 are configured to threadably engage the internal threads formed at the distal end 208 of the knob 110.

Figure 7B:
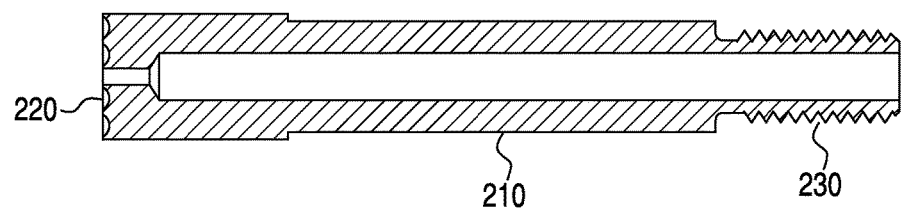
FIG. 7B is a cross-sectional view of the drive barrel taken along line 7B-7B in FIG. 7A.

FIG. 7B is a cross-sectional view of the drive barrel 210 taken along line 7A-7A (shown in FIG. 7A). FIG. 7B also shows the threads 230 formed along the proximal end of the drive barrel 210. During a process when the mechanism 100 is being cleaned, any fluid, such as water or a disinfectant, can be injected through the luer lock coupling 205, flushing out contaminants therefrom, and exiting out the flush holes 1160 defined adjacent the linear pin slots 1150 (as can been seen in FIG. 11A). Spiral ball slots 810 (FIG. 8) can be defined on the surface of a cam plate 220 formed on the distal end of the drive barrel 210. In the illustrated embodiment, the drive barrel 210 is generally hollow for the purpose of facilitating cleaning, and for reduction in material requirements.

Figure 8:
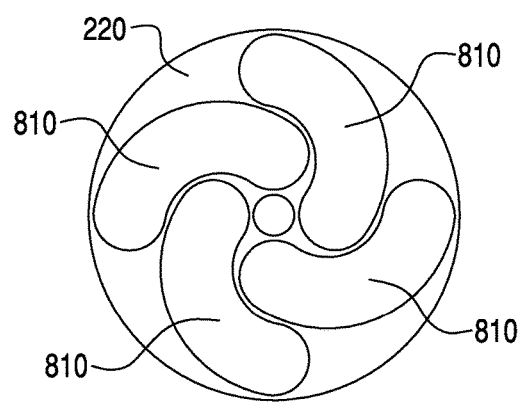
FIG. 8 is a front view of the cam plate in accordance with the disclosed subject matter.

FIG. 8 shows a front view of the cam plate 220. As discussed earlier, the cam plate 220 is formed on the distal end of drive barrel 210 and extends in a direction normal to the central axis of the drive barrel 210. The cam plate 220 can include a plurality of spiral ball slots 810 formed along the outwardly facing surface of the cam plate 220. The spiral ball slots 810 are configured to receive and engage the drive pins 150 when the cam plate 220 engages the follower plate 160 (shown in FIGS. 1 and 2). As will be described in detail below, the drive pins 150 can be fitted within the spiral ball slots 810 so that they travel within or along the spiral ball slots 810 when the drive barrel 210 is rotated. Thus, when the drive barrel 210 is rotated in a first direction, the drive pins 150 travel within the spiral ball slots 810 until the drive pins 150 extends outwardly in a direction away from the central axis of the mechanism 100. When the drive barrel 210 is rotated in an opposite direction, the drive pins 150 are retracted and travel back toward the central axis of the drive barrel 210. It should be understood that although the slots 810 are shown and described as "spiral ball slots," the slots 810 can be any shape or configuration that can receive the drive pins 150.

Figure 9:
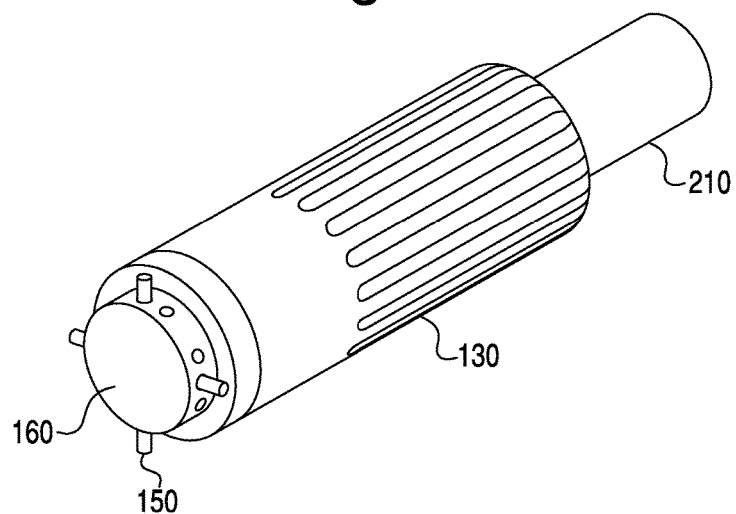
FIG. 9 is a perspective end view of the mechanism in accordance with the disclosed subject matter.

FIG. 9 shows a perspective end view of the mechanism 100 when the drive pins 150 are fully extended in a direction away from the central axis of both the mechanism 100. FIG. 9 also shows a portion of the drive barrel 210 that extends through the interior of the capture sleeve 130 with the spring capture sleeve 120 removed for clarity. The follower plate 160 can be coupled to a distal end of the capture sleeve 130. As described above, in this embodiment, the follower plate 160 is threadably coupled to the capture sleeve 130. When the follower plate 160 is coupled to the distal end of the capture sleeve 130, the drive pins 150, which are disposed within the follower plate 160, come into contact with the cam plate 220 (which is not visible in FIG. 9). As explained below in further detail, the drive pins 150 ride within the spiral ball slots 810 formed on the outwardly facing surface of the cam plate 220

Figure 10A:
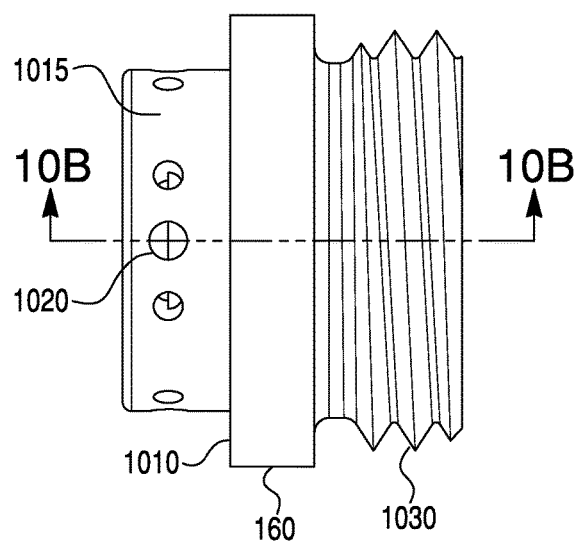
FIG. 10A is a side view of a follower plate in accordance with the disclosed subject matter.

FIG. 10A shows a side view of the follower plate 160. The follower plate 160 can include a base portion 1010, a circular end piece 1015 formed on a distal end of the follower plate 160, and threads 1030 formed on a proximal end of the follower plate 160. The threads 1030 can be configured to threadably engage the threads 610 which are formed along an interior surface of the distal end of the capture sleeve 130. In this manner, the follower plate 160 can be threadably coupled to the capture sleeve 130. As discussed above, the follower plate 160 may also be formed without threads such that the follower plate 160 is press fit within the opening defined at the distal end of the capture sleeve 130. The circular end piece 1015 also includes at least one pin opening 1020 formed along its outer surface. In the embodiment of FIG. 10A, four pin openings 1020 are formed at 90 degree increments in the outer surface of the circular end piece 1015. The pin openings 1020 are configured so that the drive pins 150 can extend through the pin openings 1020 when the drive pins 150 are extended in a direction away from the central rotational axis of the mechanism 100.

Figure 10B:
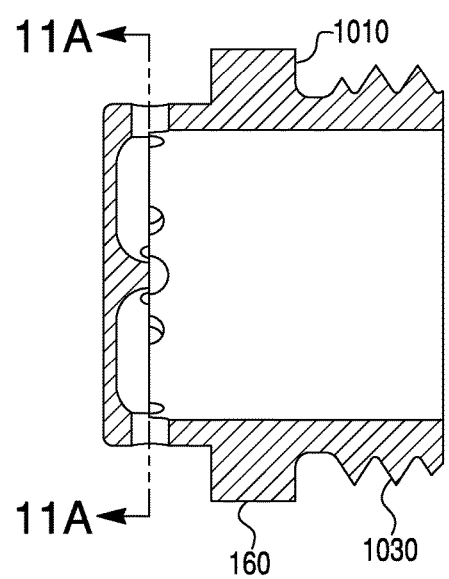
FIG. 10B is a cross-sectional view of the follower plate taken along line 10B-10B in FIG. 10A in accordance with the disclosed subject matter.
Figure 11A:
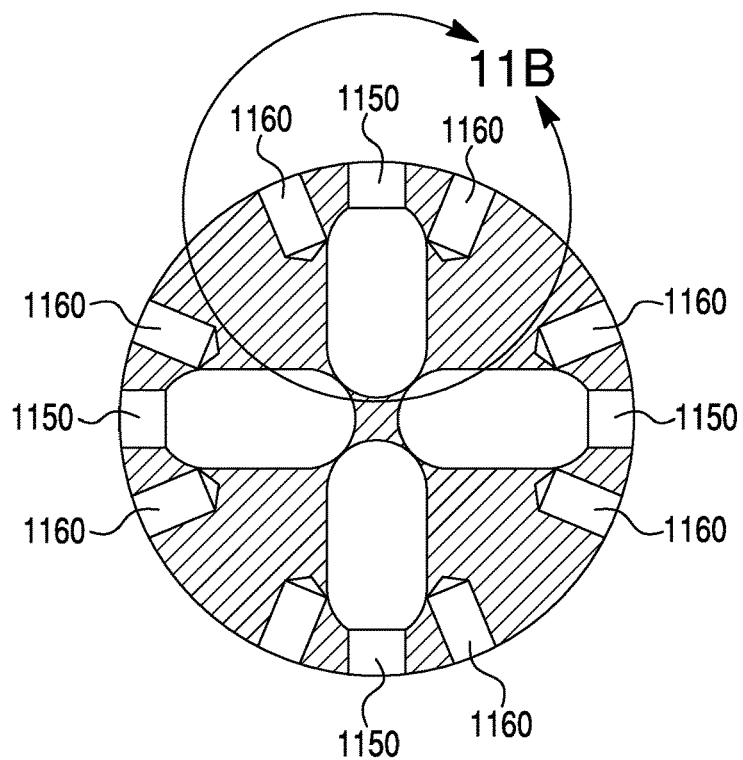
FIG. 11A is a cross-sectional view of the follower plate taken along line 11A-11A in FIG. 10B in accordance with the disclosed subject matter.

FIG. 10B shows a cross-sectional view of the follower plate 160 taken along the line 10B-10B (shown in FIG. 10A). FIG. 10B shows the base portion 1010 and the threads 1030 of the follower plate. FIG. 10B also shows the pin opening 1020 which is defined in an outer surface of the circular end piece 1015. As shown in FIG. 10B, the follower plate 160 is generally hollow to accept the drive barrel 210 shown in FIG. 7A FIG. 11A shows a cross-sectional view of the interior of the follower plate 160. A plurality of linear pin slots 1150 can be defined in an outer surface of the follower plate 160. In the embodiment of FIG. 11A, the liner pin slots 1150 are defined approximately 90 degrees apart from each other so that the follower plate 160 can accommodate four equally spaced apart drive pins 150. Thus, the drive pins 150 can be seated within the linear pin slots 1150. The linear pin slots 1150 can also be configured to allow movement of the drive pins in a direction both away from and towards the central axis of the follower plate. In this manner, during operation of the mechanism 100, the drive pins 150 can be extended in a direction away from the central axis of the mechanism 100 and retracted in a direction towards the central axis of the mechanism 100. FIG. 11A also shows a plurality of flush holes 1160 formed along the interior surface of the follower plate 160. The flush holes 1160 provide an opening for draining any fluid, such as a cleaning fluid, that is flushed through the mechanism 100. The pin slots 1150 are depicted as linear for ease of understanding and to simplify the manufacturing process, however, it is within the scope of this subject matter for the pin slots 1150 to have an oblique orientation relative to the rotational axis of the mechanism 100, as well as to be curved relative thereto.

Figure 11B:
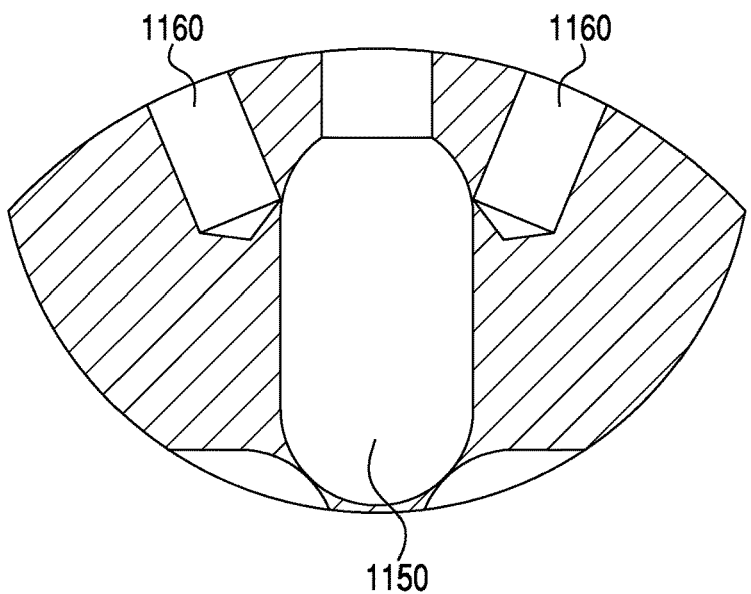
FIG. 11B is a detailed view of a portion of the follower plate in FIG. 11A in accordance with the disclosed subject matter.

FIG. 11B shows a detailed view of the portion A from FIG. 11A. FIG. 11B shows one of the linear pin slots 1150 disposed between a pair of the flush holes 1160 which act as drains for removal of fluids passing through the body of the mechanism 100.

Figure 12:
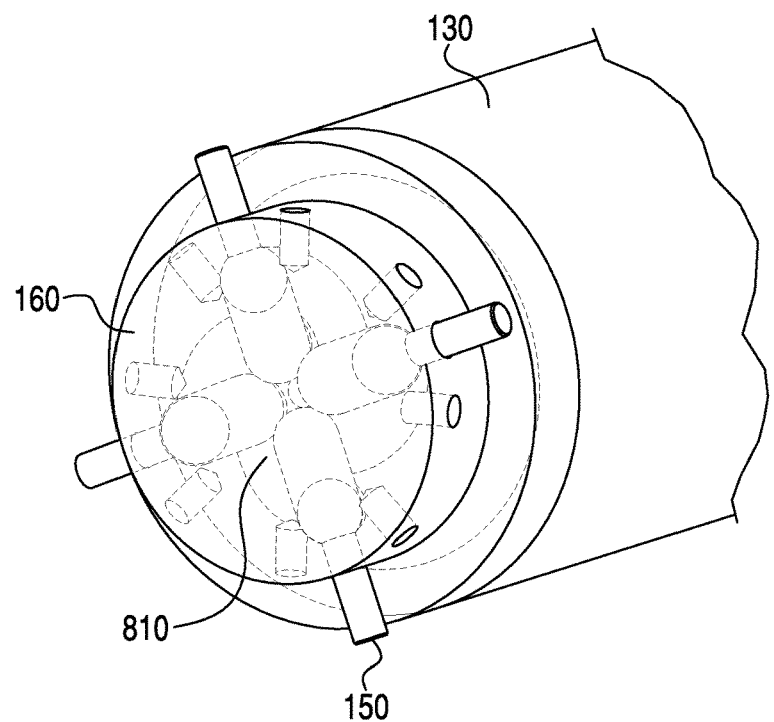
FIG. 12 is an isometric view showing the distal end of the mechanism in accordance with the disclosed subject matter.

FIG. 12 is an isometric view showing the distal end of the mechanism 100. The capture sleeve 130 is shown with the follower plate 160, which is shown in an isometric, transparent view so as to illustrate the relationship between the cam plate 220 and the follower plate, fitted to the distal end of the capture sleeve 130. FIG. 12 also shows the drive pins 150 which are fitted within the follower plate 160 and which engage the spiral ball slots 810. FIG. 12 shows the drive pins 150 in a fully extended position.

Figure 13:
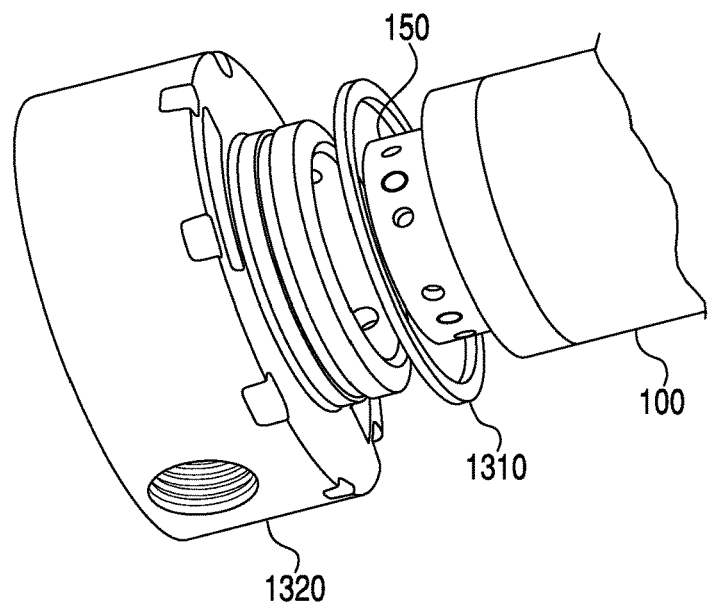
FIG. 13 shows the mechanism used in a manner to remove an external retaining ring in accordance with the disclosed subject matter.

FIG. 13 shows the mechanism 100 used in a manner to remove a retaining ring 1310 from a fitting 1320. The mechanism 100 can be fitted into an opening of the fitting 1320. A user can then rotate the knob portion 110 causing the drive pins 150 to extend in a direction away from the central axis of the mechanism 100. The drive pins 150 which are retracted and not visible in FIG. 13, engage the ring 1310 allowing the user to remove the ring 1310 by actuating the mechanism 100 and then moving the ring 1310 away from fitting 1320 while the mechanism is actuated. This permits hands free removal of the retaining ring 1310 from the fitting 1320. The mechanism can likewise be used to insert the retaining ring 1310. Thus, the mechanism 100 can used as an internal spanner wrench thus allowing insertion and removal of an object without damaging adjacent internal finishes.

Figure 14A:
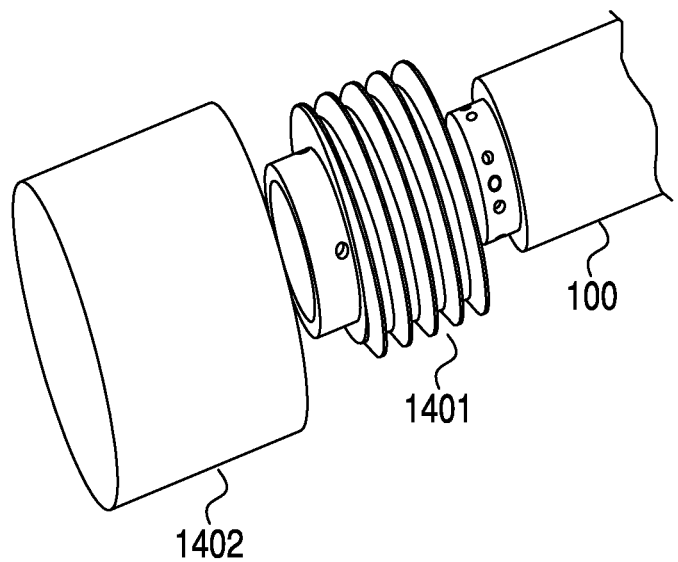
FIG. 14A illustrates use of the tool configured as a non-marring bushing inserter prior to engaging a bushing.
Figure 14B:
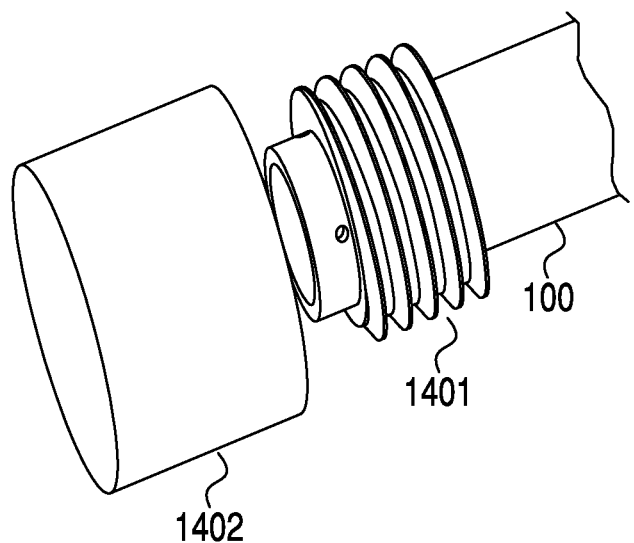
FIG. 14B illustrates use of the tool configured as a non-marring bushing inserter while engaging a bushing.

FIGS. 14A and 14B illustrate another exemplary application for the mechanism 100 which can be used as a non-marring bushing inserter. FIG. 14A shows the mechanism before it engages a bushing 1401 for placement into a fitting 1402. In FIG. 14A, the driving pins 150 are retracted so that the mechanism 100, and more specifically, the follower plate 160 can be placed in an opening formed in the bushing 1401. Once the mechanism 100 is placed inside the opening of the bushing 1401, as shown in FIG. 14B, the drive pins 150 can be extended so that they move in a direction away from the central axis of the mechanism 100. This causes the drive pins 150 to engage the interior surface of the bushing 1401 so that the bushing 1401 can be manipulated for placement into the fitting 1402. The non-marring bushing inserter concept disclosed herein could be used in a variety of other applications, such as for robotic gripper arms where drive pins are activated utilizing the mechanisms described above.

The components of the mechanism 100 described above, such as the knob portion 110, the spring capture sleeve 120, the capture sleeve 130, the follower plate 160, the luer lock 205 and the drive barrel 210 may be hollow to facilitate sterilization and cleaning of the mechanism 100. In this embodiment, a liquid, such as a cleaning solution could enter the mechanism 100 through the luer lock 205 located at the proximal end of the mechanism 100 and then exit through the flush hole(s) 1160 formed at the distal end of the mechanism 100. It should be understood that in another embodiment, the components of the mechanism could be formed as solid components. The irrigation ports in the cam follower 160 could also be used for lubrication of the internal components when sterilization is not required. In another embodiment, certain of the components could be formed as a unitary structure.

The mechanism described above includes a plurality of threaded surfaces that are formed to receive and or engage the various structures described above. For example, as described above, the luer lock 205 and the capture sleeve 130 include threads along their respective interior surfaces for receiving a threaded component, while the drive barrel 210 and the follower plate 160 have exterior threads for engaging the interior threads of the luer lock 205 and the capture sleeve 130, respectively. However, it should be understood that in accordance with other embodiments of the disclosed subject matter, the orientation of the interior and exterior threads as between the components could be reversed. It should also be understood that embodiments of the disclosed subject matter also contemplate other systems for mating and/or attaching the various components of the mechanism 100. For example, the various components could be press fit into one another. Alternatively, the components could be formed as a unitary structure, which would eliminate the need to provide structures for joining the structures together.

The disclosed embodiments also contemplate that the spiral ball slots 810 and the linear ball slots 1150 could be reversed so that the spiral ball slots 810 are formed on a surface of that is currently the follower plate 160 and the linear pin slots 1150 could be formed on the surface of that is currently cam plate 220. In other words, in such an embodiment, the location of the cam plate 220 can be interchanged with the location of the follower plate 160.

The disclosed embodiments also contemplate a variety of shapes for the driving pins 150. Any known shape could be incorporated into the mechanism to the extent that such shapes could still extend through the follower plate 160 and be engaged by the spiral ball slots 810. It should also be understood that the spiral ball slots 810 could be formed in any shape or configuration, such as, but not limited to grooves or openings, which can receive the pins 150.

The disclosed embodiments contemplate a variety of materials that can be used for the mechanism 100, including but not limited to various plastics, polymers, metals, composites, etc., including shape memory alloys, stainless steels, and the like.

Figure 15:
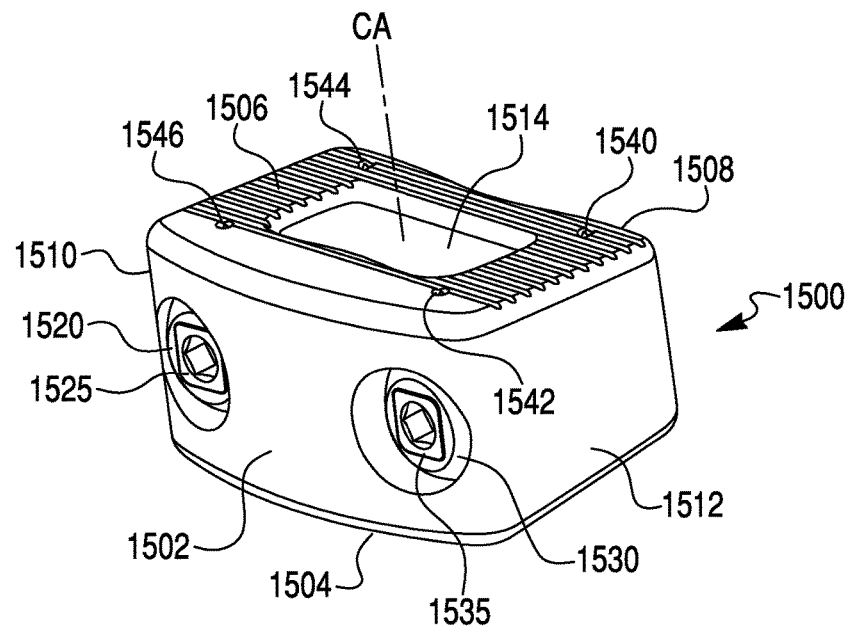
FIG. 15 is a perspective view showing an anterior perspective view of one exemplary embodiment of a spinal interbody device and system which incorporates a drive mechanism for extending and retracting one or more locking projections.

FIG. 15 shows an anterior perspective view of one exemplary embodiment of a spinal interbody device and system 1500 which incorporates a drive mechanism for extending and retracting one or more locking projections. The interbody device 1500 can be formed, for example, as a cage that can be molded, machined, printed, or otherwise formed as a single continuous structure. Alternatively, the interbody device 1500 can comprise a plurality of separate structures that are attached, adhered, or otherwise assembled together. The interbody device 1500 can be configured as a generally cuboid structure suitable for placement between adjacent vertebrae. The interbody device 1500 can also be shaped so as to provide restoration of disc height when placed between vertebrae and to generally mimic the spacing and structure of an intervertebral disk in this region.

The interbody device 1500 can be configured for use in many different medical and surgical procedures, including to create opportunities for spinal fusion in cases of degenerative instability, post-discectomy syndrome, post-traumatic instability, and other diseases, injuries, or malformations in the spine.

As shown in FIG. 15, the interbody device 1500 can include a front surface 1502, a lower surface 1504, an upper surface 1506 opposed to the lower surface 1504, a rear surface 1508 opposed to the front surface 1502, a first lateral surface 1510, and a second lateral surface 1512 opposed to the surface 1510. Each of the surfaces 1502-1512 can be immediately adjacent to each other to form the entire exterior facing surface of the interbody device 1500. The front surface 1502 can have an outermost periphery shaped as a substantial rectangle, and the rear surface 1508 can also have an outermost periphery shaped as a substantial rectangle, although smaller than the rectangle of the front surface 1502 in this embodiment.

The interbody device 1500 can include an opening 1514 that extends from the upper surface 1506 to the lower surface 1504. The opening 1514 can include a central axis CA that extends vertically through the entirety of the interbody device 1500. The opening 1514 can be configured to receive tissue, bone growth tissue or materials, ceramic materials, adhesives, regenerative materials, or other substances determined to be appropriate for a given procedure.

FIG. 15 also shows a first front cam plate 1520 and a second front cam plate 1530 disposed on the front surface 1502 of the interbody device 1500. A first drive mechanism head 1525 is disposed within the first front cam plate 1520 and a second drive mechanism head 1535 is disposed within the second front cam plate 1530. Slots are formed within the first and second drive mechanism heads 1525 and 1530 and these slots are configured to receive a driving tool, such as a hex screw driver, which can engage the slots and provide friction or locking for causing rotation of the drive mechanism heads 1525 and 1535 when the driver is rotated, which in turn causes rotation of the cam plates 1520 and 1530. The operation of the drive mechanism is described in greater detail below.

FIG. 15 also shows openings 1540, 1542, 1544 and 1546 formed on the upper surface 1506 of the interbody device 1500. As will be described in greater detail below, the openings 1540-1546 can allow locking projections to extended therethrough. Additional openings are formed on the lower surface 1504 of the interbody device 1500.

Figure 16:
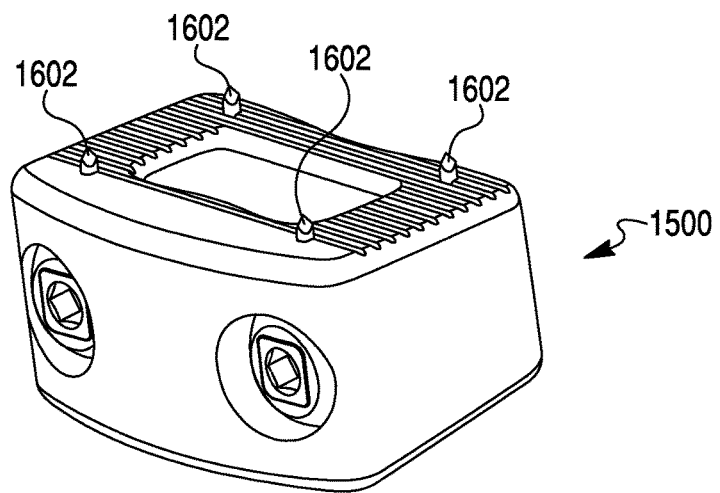
FIG. 16 is a perspective view of the spinal interbody device with the locking projections partially extended.

FIG. 16 shows the interbody device 1500 with locking projections 1602 extending through the openings 1540, 1542, 1544, 1546. As will be described in greater detail below, the locking projections 1602 can be extended and retracted via rotation of the drive mechanism heads 1525 and 1535.

Figure 17:
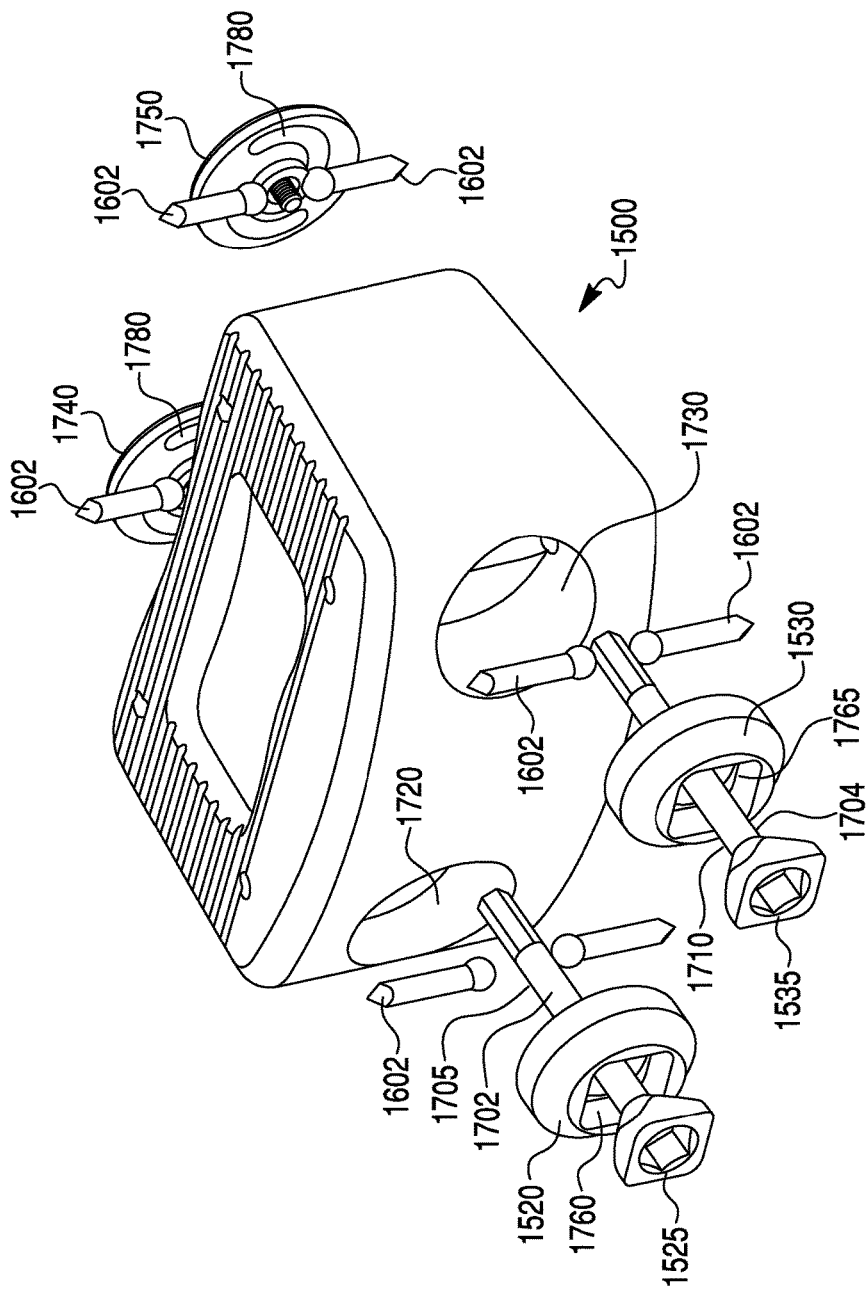
FIG. 17 is an exploded perspective view of the spinal interbody device.

FIG. 17 is an exploded perspective view of the interbody device 1500 showing a first front opening 1720 and second front opening 1730 formed within the interbody device 1500. The first front opening 1720 can receive first front cam plate 1520 and the second front opening 1730 can receive the second front cam plate 1530. Rear openings (not shown) are also formed in the rear surface 1508 of the interbody device 1500 and can each be formed as an extension throughway from respective openings 1720, 1730 that extend along an axis substantially perpendicular to the central axis CA of the device 1500 and entirely through the device (with or without intersection with opening 1514). The rear openings are configured to receive a first rear cam plate 1740 and a second rear cam plate 1750. Each of the front and rear openings have slots (not visible in FIG. 17) which are configured to receive the locking projects 1602. The locking projections 1602 of the embodiment of FIG. 17 are formed as pins that have a substantial spherical bulb at one end and a sharpened tip at an opposing end that can extend outside of a plane that substantially contains the upper surface 1506.

FIG. 17 also shows a first drive mechanism 1705 and a second drive mechanism 1710. The first drive mechanism 1705 includes the first drive mechanism head 1525 and a first drive rod 1702 and the second drive mechanism 1710 includes the second drive mechanism head 1535 and the second drive rod 1704. The first drive mechanism 1705 is fitted within an opening 1760 formed within the first front cam plate 1520. In particular, the first drive mechanism head 1525 is fitted within the first front cam plate 1520 in a locking configuration such that rotation of the drive rod 1702 also results in rotation of the first front cam plate 1520. The first drive rod 1702 also can extend entirely through the interbody device 1500 via the first front opening 1720. The first drive rod 1702 extends through the entire interbody device 1500 so that it can also engage the first rear cam plate 1740. Rotation of the first drive mechanism head 1525 causes rotation of the first front cam plate 1520, the first drive rod 1702 and the first rear cam plate 1740.

Similarly, FIG. 17 also shows that the second drive mechanism 1710 is fitted within an opening 1765 formed within the second front cam plate 1530. In particular, the second drive mechanism head 1535 is fitted within the second front cam plate 1530 so that the second drive rod 1704 extends through the interbody device 1500 via the second front opening 1730. The second drive rod 1704 extends through the entire interbody device 1500 so that it can engage the second rear cam plate 1750. Rotation of the second drive mechanism head 1535 causes rotation of the second front cam plate 1530, the second drive rod 1704 and the second rear cam plate 1750.

Each of the first and second front cam plates 1520 and 1530 and the first and second rear cam plates 1740 and 1750 can include a plurality of camming grooves, such as spiral ball slots 1780, that are configured to receive and engage the ball or spherical shaped portions of the locking projections 1602. The front openings 1720 and 1730 as well as the rear openings, include a plurality of camming grooves, such as linear pin slots formed therein, for retaining and guiding the ball or spherical shaped portions of the locking projections 1602 during actuation of the first and second drive mechanisms 1705 and 1710.

As will be described in greater detail below, when the first and second drive mechanism 1705 and 1710 are actuated, through, for example, rotation of the first and second drive mechanism heads 1525 and 1535, the first and second front cam plates 1520 and 1530 and the first and second rear cam plates 1740 and 1750 all rotate. This causes the spiral ball slots 1780 to engage the ball or spherical shaped portions of the locking projections 1602 when the cam plates (1520, 1530, 1740, 1750) are rotated, the ball or spherical shaped portions of the locking projections 1602 then are caused by the moving spiral ball slots 1780 to slide within and engage the respective linear ball slots formed within the body of the interbody device 1500. The locking projections 1602 can be fitted within the spiral ball slots 1780 so that the ball or spherical shaped portions ride within the spiral ball slots 1780 when the drive mechanisms 1705 and 1710 are rotated. Thus, when the drive mechanisms 1705 and 1710 are rotated in a first direction, the ball or spherical shaped portions of the locking projections 1602 ride within the spiral ball slots 1780 until the locking projections 1602 extend through the upper and lower surfaces 1506, 1504, of the interbody device 1500. When the drive mechanisms 1705 and 1710 are rotated in an opposite direction, the locking projections 1602 are retracted through the upper and lower surfaces 1506, 1504 into the interbody device 1500.

Figure 18:
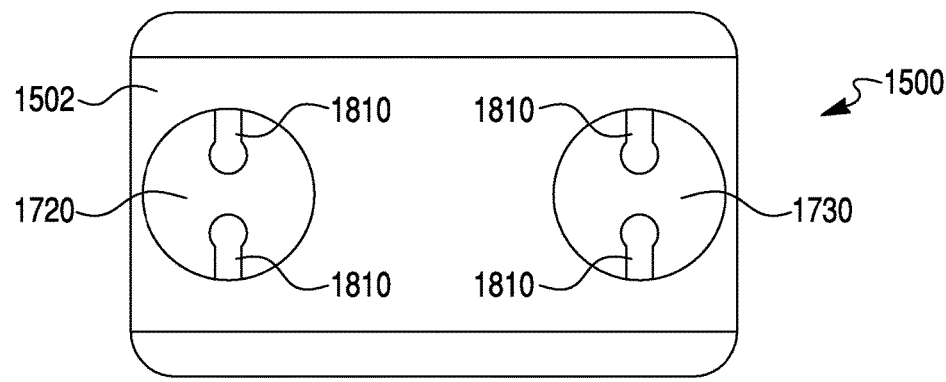
FIG. 18 is a front view of the interbody device.

FIG. 18 shows a front view of the interbody device 1500, including the front surface 1502, as well as the first opening 1720 and the second opening 1730, which are defined in the front surface 1502. As described above, the first and second openings 1720 and 1730 are configured to receive the first front cam plate 1520 and the first drive mechanism 1705, and the second front cam plate 1530 and second drive mechanism 1710, respectively. Also, as shown in FIG. 18, interior ball slots 1810 are formed or provided at or on an interior surface of the interbody device 1500 within the openings 1720 and 1730. In the embodiment of FIG. 18, the interior ball slots 1810 can be formed at about 180 degree increments away from each other so that they can accommodate two equally spaced apart locking projections 1602. Thus, the locking projections 1602 can be seated within the linear ball slots 1810. The linear ball slots 1810 can also be configured to allow movement of the locking projections 1602 in a direction both away from and towards the drive rod 1704. In this manner, during actuation of the drive mechanisms 1705 and 1710, the locking projections 1602 can be extended in a direction through the upper and lower surfaces and away from the interbody device 1500 as well as retracted back through the upper and lower surfaces to a location completely or partially interior of the interbody device 1500, i.e., between the upper and lower surfaces 1506, 1504.

Figure 19:
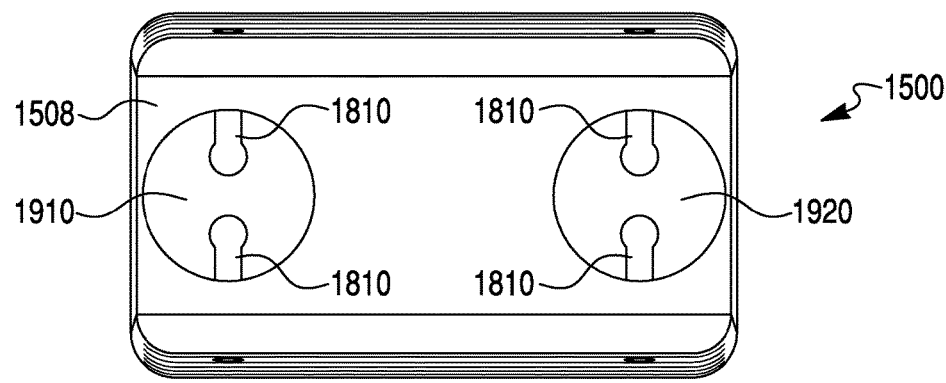
FIG. 19 is a rear view of the interbody device.

FIG. 19 shows a rear view of the interbody device 1500, including the rear surface 1508, as well as a first rear opening 1910 and a second rear opening 1920, which are disposed on the rear surface 1508. The first and second rear openings 1910 and 1920 are configured to receive the first rear cam plate 1740 and the second rear cam plate 1750, respectively. The first drive rod 1702 also passes through the first rear opening 1910 and engages the first rear cam plate 1740 and the second drive rod 1704 passes through the second rear opening 1920 and engages the second rear cam plate 1750. Also, as shown in FIG. 19, interior ball slots 1810 can be formed on or placed in an interior surface of the interbody device 1500 within the rear openings 1910 and 1920. In the embodiment of FIG. 19, the interior ball slots 1810 can be formed at about 180 degree increments away from each other so that they can accommodate two equally spaced apart locking projections 1602. Thus, the locking projections 1602 can be seated within the linear ball slots 1810. The linear ball slots 1810 can also be configured to allow movement of the locking projections 1602 in a direction both away from and towards the drive rod 1704. In this manner, during actuation of the drive mechanisms 1705 and 1710, the locking projections 1602 can be extended in a direction through the upper and lower surfaces and away from the interbody device 1500 as well as retracted back through the upper and lower surfaces to a location completely or partially interior of the interbody device 1500.

Figure 20:
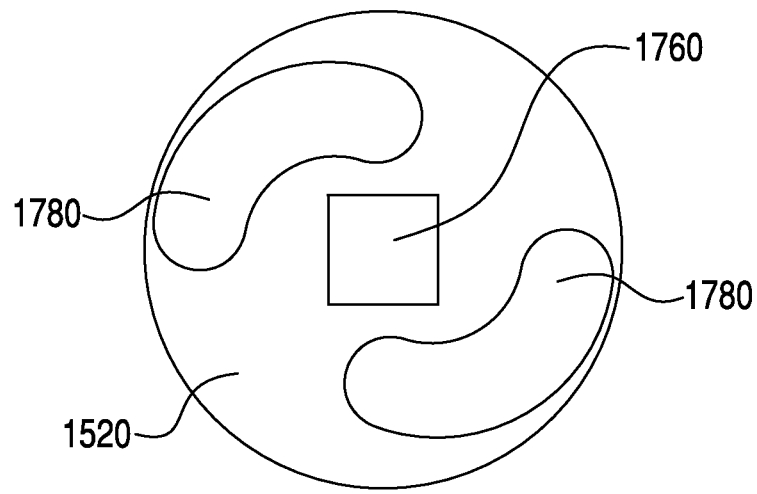
FIG. 20 is a front view of a front cam plate of the interbody device.

FIG. 20 shows a front view of the first front cam plate 1520. The first front cam plate 1520 includes the opening 1760 for receiving the first drive mechanism 1705 and two spiral ball slots for 1780 formed along a top surface of the cam plate 1520. The spiral ball slots 1780 are configured to receive and engage the locking projections 1602 when the cam plate 1520 and the linear ball slot 1810 formed in the opening 1720 sandwich the locking projection 1602 therebetween. The locking projections 1602 can be fitted within the spiral ball slots 1810 so that they ride within the spiral ball slots 1810 when the drive mechanism 1705 is rotated. Thus, when the drive mechanism 1705 is rotated in a first direction, the locking projections 1602 ride within the spiral ball slots 1780 and linear slots 1810 until the locking projections 1602 extend outwards in a direction away from an upper and lower surface, respectively, of the interbody device 1500.

It should be understood that the second front cam plate 1530 can have the same structure as the first front cam plate 1520 such that the second front cam plate 1530 interacts with locking projections 1602 and the linear ball slots 1810 of the second opening 1730 in the same manner that the first front cam plate 1520 interacts with the locking projections 1602 and linear ball slots 1810 formed in the interior of the first opening 1720.

Figure 21:
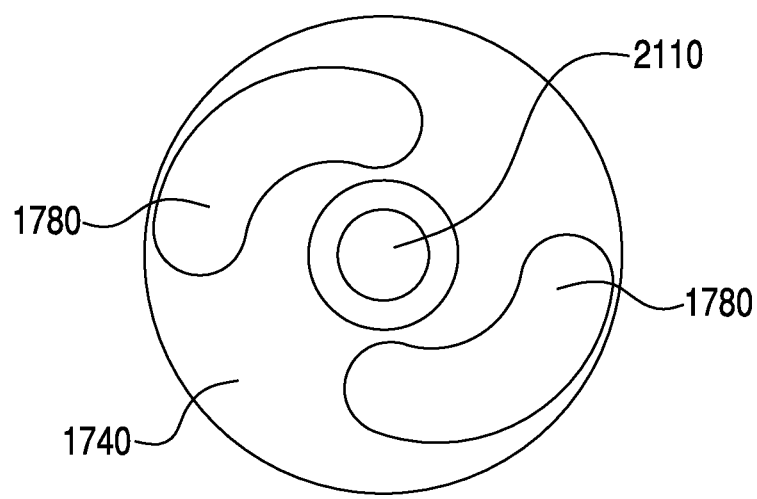
FIG. 21 is a front view of a rear cam plate of the interbody device.

FIG. 21 shows a front view of the first rear cam plate 1740. The first rear cam plate 1740 includes pin 2010 for engaging the drive rod 1702 so that rotation of the drive mechanism 1705 and drive rod 1702 also causes rotation of the first rear cam plate 1740. FIG. 21 also shows that the first rear cam plate 1740 also includes two spiral ball slots 1780 formed along the top surface of the cam plate 1740. The spiral ball slots 1780 are configured to receive and engage the locking projections 1602 when the cam plate 1740 and the linear ball slots 1810 formed in the opening 1910 sandwich the locking projections 1602 therebetween. The locking projections 1602 can include a spherical bulb (or other mating surface) at one thereof that can be fitted and ride within the spiral ball slots 1780 so that the projections 1602 ride within the spiral ball slots 1780 when the drive mechanism 1705 is rotated. Thus, when the drive mechanism 1705 is rotated in a first direction, the locking projections 1602 ride within the spiral ball slots 1780 and liner slots 1810 until a sharp end of the locking projections 1602 extend outwards away from the upper and lower surfaces of the interbody device 1500.

Figure 22:
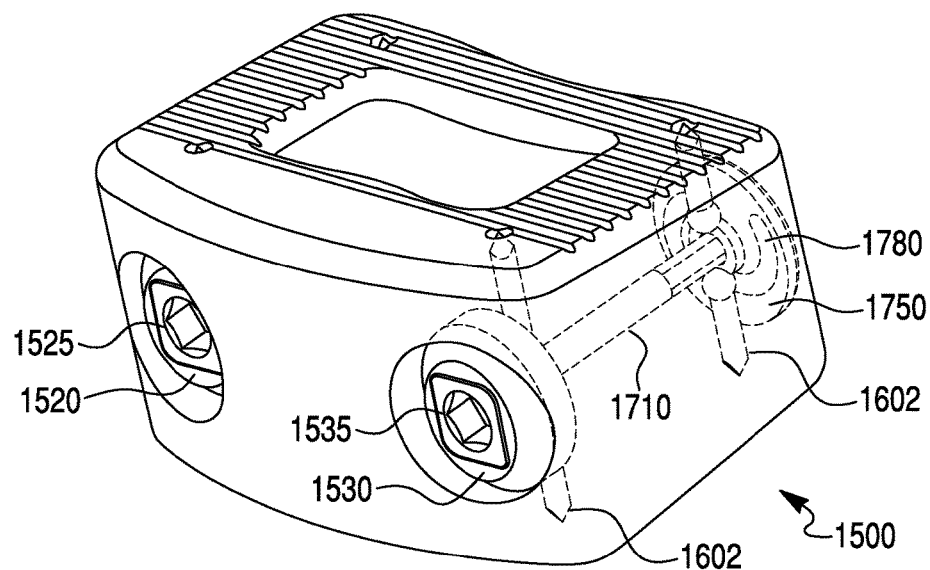
FIG. 22 is a perspective view with a partial view of hidden structures of the spinal interbody device in a retracted state.

FIG. 22 shows a perspective view of the interbody device 1500, including a partial view of hidden structures of the spinal interbody device 1500 while in a retracted state. FIG. 22 shows that while in a retracted state, the locking projections 1602 are maintained within the interbody device 1500 so that they are not visible to a user. FIG. 22 also shows the second drive mechanism 1710 which includes the second drive mechanism head 1535. FIG. 22 also shows the second front cam plate 1530 and the second rear cam plate 1750. As described earlier, rotation of the second drive mechanism head 1535 causes rotation of the second front cam plate 1530 and the second rear cam plate 1750 via the drive mechanism 1710. FIG. 22 also shows the spiral ball slots 1780 that are configured to receive and engage the ball or spherical shaped portions of the locking projections 1602.

Figure 23:
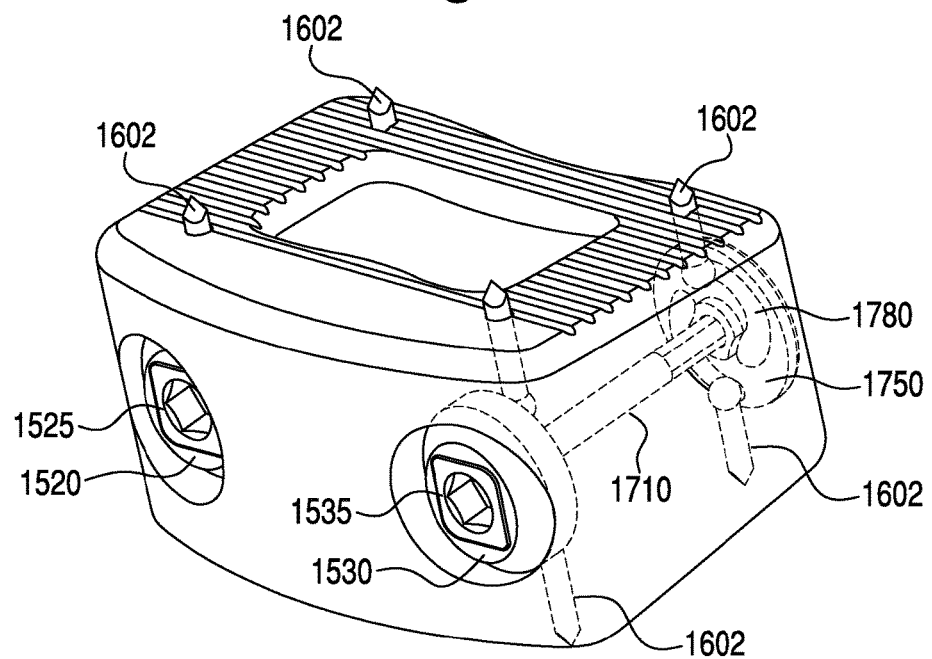
FIG. 23 is a perspective view with a partial view of hidden structures of the spinal interbody device in an extended state.

FIG. 23 is a perspective view with a partial view of hidden structures of the spinal interbody device while in an extended state. As was described earlier, the locking projections 1602 are placed in an extended state when the first and second drive mechanism 1705 (not visible in FIG. 23) and 1710 are actuated, through, for example, rotation of the first and second drive mechanism heads 1525 and 1535, the first and second front cam plates 1520 and 1530 and the first and second rear cam plates 1740 (not visible in FIG. 23) and 1750 all rotate. This causes the spiral ball slots 1780 to engage the ball or spherical shaped portions of the locking projections 1602 when the cam plates (1520, 1530, 1740 (not visible in FIG. 23), 1750) are rotated, the ball or spherical shaped portions of the locking projections 1602 then are caused by the moving spiral ball slots 1780 to slide within and engage the respective linear ball slots formed within the body of the interbody device 1500.

It should be understood that the second rear cam plate 1750 can have the same structure as the first rear cam plate 1740, such that the second rear cam plate 1750 interacts via projections 1602 with the linear ball slots 1810 of the second rear cam plate 1750 in the same manner that the first rear cam plate 1740 interacts via the projections 1602 with the linear ball slots 1810 formed in the interior of the opening 1920.

As described above, rotation of the first and second drive mechanisms 1705 and 1710 in a first direction causes the locking projections 1602 to extend in a direction away from the interbody device 1500, while rotation of the first and second drive mechanisms 1705 and 1710 in a second direction causes the locking projections 1602 to retract within the interbody device 1500. The locking projections 1602 can be used to assist frictional connection to vertebrae during initial placement of the interbody device 1500 as well as assist in long term prevention of migration of the interbody device 1500 with respect to adjacent vertebrae and enhance implant stability, especially under axial torsion loading. The locking projections 1602 can be formed as a spike shaped element as shown or any other structure capable of forming a frictional connection to vertebrae.

It should be noted that the locking projections 1602 can serve several different functions. For example, locking projections 1602 can enhance implant stability, and can also facilitate radiologic identification and orientation of the interbody device 1500 in a surgical space, such as between adjacent vertebrae. With respect to the function of identification and orientation, the locking projections 1602 can be made from radio-opaque material(s) such that they serve as a posterior X-ray marker for the device 1500. Thus, under X-ray, the locking projections 1602 are visible while the interbody device 1500 may be transparent.

With respect to the function of implant stability, one locking projection 1602 can be provided in order to enhance implant stability, especially under axial torsion loading.

The disclosed embodiments also contemplate that the spiral ball slots 1780 and the linear pin slots 1810 could be reversed so that the spiral ball slots 1780 are formed or provided at or on a surface of the opening formed within the interbody device, such as the opening 1720, and the linear pin slots 1810 could be formed or located on the surface that is currently a cam plate, such as first front cam plate 1520.

The disclosed embodiments also contemplate a variety of shapes for the locking projections 1602. Any known shape could be incorporated into the mechanism to the extent that such shapes could still be engaged by the spiral ball slots 1780 and the linear pin slots 1810.

The disclosed embodiments contemplate a variety of materials that can be used for the mechanism 1500, as well as the drive mechanisms 1705, 1710, and the cam plates 1520, 1530, 1740 and 1750, including but not limited to various plastics, polymers, metals, composites, etc., including shape memory alloys, stainless steels, and the like.

While the subject matter has been described in detail with reference to exemplary embodiments thereof, it will be apparent to one skilled in the art that various changes can be made, and equivalents employed, without departing from the scope of the invention. All related art references described above are hereby incorporated by reference in their entirety.

What is claimed is:

1. A spinal interbody device, comprising:
    a front surface;
    a rear surface substantially opposed to the front surface;
    an upper surface connected to the front surface and the rear surface;
    a lower surface opposed to the upper surface and connected to each of the front surface and the rear surface;
    at least one opening formed at the front surface, the at least one opening extending through the front surface;
    at least one projection; and
    a drive mechanism disposed adjacent the at least one opening and configured to move the at least one projection so that the at least one projection moves through at least one of the upper surface and the lower surface, the drive mechanism including a cam plate,
    wherein the at least one opening formed at the front surface includes at least one first camming groove and the cam plate includes at least one second camming groove defined therein for retaining and guiding the at least one projection when the front surface is disposed adjacent to the cam plate, and at least one of the first camming groove and second camming groove is a spiral slot.

2. The spinal interbody device according to claim 1, wherein at least one of the first camming groove and second camming groove comprises
    a linear ball slot located in one of the front surface and the cam plate, wherein
    the spiral slot and linear ball slot are configured for engaging the at least one projection, and wherein the cam plate includes a front cam plate.

3. The spinal interbody device according to claim 2, wherein the spiral slot is defined in the front cam plate and the linear ball slot is defined in the at least one opening formed in the front surface of the interbody device.

4. The spinal interbody device according to claim 3, wherein the at least one projection is in the spiral slot and the linear ball slot.

5. The spinal interbody device according to claim 2, further comprising at least one opening formed in the rear surface of the interbody device, wherein the cam plate further comprises at least one rear cam plate received in the at least one opening formed in the rear surface of the interbody device, and wherein the rear cam plate and the at least one opening formed in the rear surface of the interbody device include at least one third camming groove.

6. The spinal interbody device according to claim 5, wherein at least one linear ball slot is defined in the at least one opening formed in the rear surface of the interbody device and the at least one rear cam plate includes at least one spiral slot defined therein.

7. The spinal interbody device according to claim 5, further comprising a drive bar that engages both the rear cam plate and the front cam plate.

8. The spinal interbody device according to claim 2, wherein the at least one linear ball slot includes a plurality of linear ball slots.

9. The spinal interbody device according to claim 2, wherein the at least one spiral slot includes a plurality of spiral ball slots.

10. The spinal interbody device according to claim 2, wherein the spiral slot follows an arcuate path.

11. The spinal interbody device according to claim 2, wherein the spiral slot includes at least one slot for receiving the at least one projection.

12. The spinal interbody device according to claim 11, wherein the spiral slot has a width greater than or equal to a largest width of the at least one projection so that the spiral slot can receive the at least one projection.

13. The spinal interbody device according to claim 2, wherein the front cam plate has a rotational axis and wherein the at least one projection extends in direction normal to the rotational axis of the front cam plate when the front cam plate is rotated in a first direction causing the at least one projection to enter an extended state.

14. The spinal interbody device according to claim 1, wherein the at least one opening extends through the interbody device to the rear surface and the drive mechanism includes a drive bar that extends from the at least one opening disposed on the front surface of the interbody device to the rear surface of the interbody device.

15. The spinal interbody device according claim 1, wherein the at least one projection includes a bulb and a columnar structure extending from the bulb.

16. The spinal interbody device according to claim 1, wherein rotation of the drive mechanism in a first direction cause the at least one projection to enter an extended state, and rotation of the drive mechanism in a second direction that is different from the first direction causes the at least one projection to enter a non-extended slate.

17. The spinal interbody device according to claim 1, wherein the drive mechanism includes a head having a slot configured to engage a driving tool.

\* \* \* \* \*